United States Patent
Nishii

(10) Patent No.: US 10,631,805 B2
(45) Date of Patent: Apr. 28, 2020

(54) X-RAY IMAGING SYSTEM, INFORMATION PROCESSING METHOD, AND COMPUTER READABLE MEDIUM

(71) Applicant: CANON KABUSHIKI KAISHA, Tokyo (JP)

(72) Inventor: Yuichi Nishii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 220 days.

(21) Appl. No.: 15/426,310

(22) Filed: Feb. 7, 2017

(65) Prior Publication Data
US 2017/0251989 A1    Sep. 7, 2017

(30) Foreign Application Priority Data
Mar. 3, 2016    (JP) .................................. 2016-041311

(51) Int. Cl.
*A61B 6/00* (2006.01)

(52) U.S. Cl.
CPC .............. *A61B 6/461* (2013.01); *A61B 6/563* (2013.01); *A61B 6/566* (2013.01)

(58) Field of Classification Search
None
See application file for complete search history.

(56) References Cited

U.S. PATENT DOCUMENTS

| | | | |
|---|---|---|---|
| 7,206,840 B2 | 4/2007 | Choi et al. | |
| 8,400,938 B2 | 3/2013 | Matsuura | |
| 8,675,624 B2 | 3/2014 | Tachikawa et al. | |
| 9,462,992 B2 | 10/2016 | Tachikawa et al. | |
| 9,973,988 B2 | 5/2018 | Ando | |
| 10,172,053 B2 | 1/2019 | Ando | |
| 2002/0188723 A1 | 12/2002 | Choi et al. | |
| 2006/0082489 A1* | 4/2006 | Liu | H04B 17/345 342/52 |

(Continued)

FOREIGN PATENT DOCUMENTS

| | | |
|---|---|---|
| CN | 1462523 A | 12/2003 |
| CN | 101902768 A | 12/2010 |

(Continued)

OTHER PUBLICATIONS

Office Action dated Aug. 23, 2019, in counterpart application CN 201710108334.4 (17 pages).

(Continued)

*Primary Examiner* — Hoon K Song
(74) *Attorney, Agent, or Firm* — Venable LLP

(57) ABSTRACT

Provided is an X-ray imaging system, including: an imaging apparatus configured to receive an X-ray beam to form an image; a control apparatus; a determination unit configured to determine whether or not interference with a specific device is detected in a channel used for wireless communication between at least one of the imaging apparatus or the control apparatus, and a master apparatus; and an output unit configured to output, when the interference is determined to have been detected and the wireless communication is stopped, notification information including a notification that the wireless communication is stopped, the imaging apparatus and the control apparatus being configured to communicate to/from each other via the wireless communication.

8 Claims, 8 Drawing Sheets

(56) References Cited

U.S. PATENT DOCUMENTS

| | | | |
|---|---|---|---|
| 2009/0040989 A1* | 2/2009 | da Costa | H04L 41/0806 370/338 |
| 2010/0302966 A1 | 12/2010 | Matsuura | |
| 2011/0052016 A1 | 3/2011 | Nishii | |
| 2011/0116486 A1 | 5/2011 | Tachikawa et al. | |
| 2012/0177183 A1* | 7/2012 | Liu | A61B 6/4405 378/91 |
| 2013/0129048 A1* | 5/2013 | Chicchetti | H05G 1/08 378/62 |
| 2014/0177806 A1 | 6/2014 | Tachikawa et al. | |
| 2016/0174927 A1* | 6/2016 | Ohguri | A61B 6/4233 348/77 |
| 2017/0238219 A1* | 8/2017 | Ando | H04W 36/20 455/501 |
| 2018/0234899 A1 | 8/2018 | Ando | |

FOREIGN PATENT DOCUMENTS

| | | |
|---|---|---|
| CN | 102076119 A | 5/2011 |
| JP | 5708645 B2 | 4/2015 |
| JP | 2017-143940 A | 8/2017 |
| WO | 2011/142162 A1 | 11/2011 |

OTHER PUBLICATIONS

Office Action dated Nov. 12, 2019, in counterpart application JP 2016-041311 (8 pages).

* cited by examiner

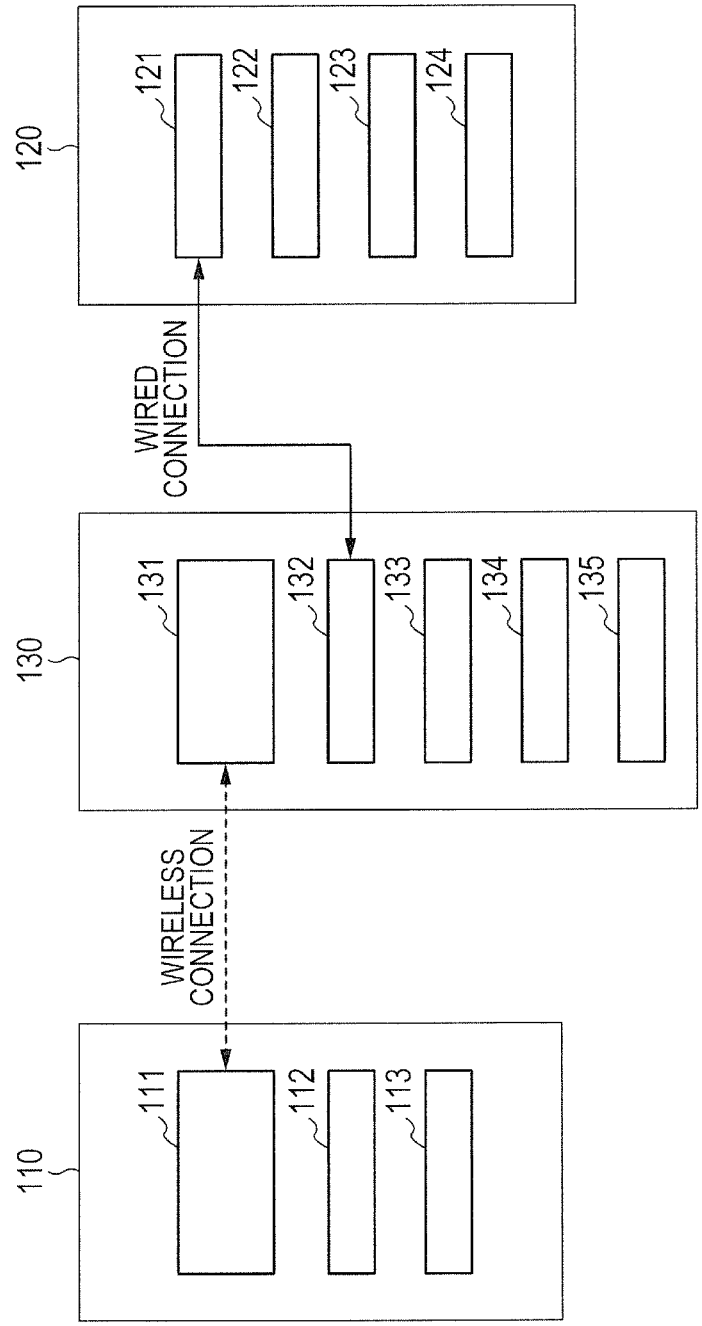

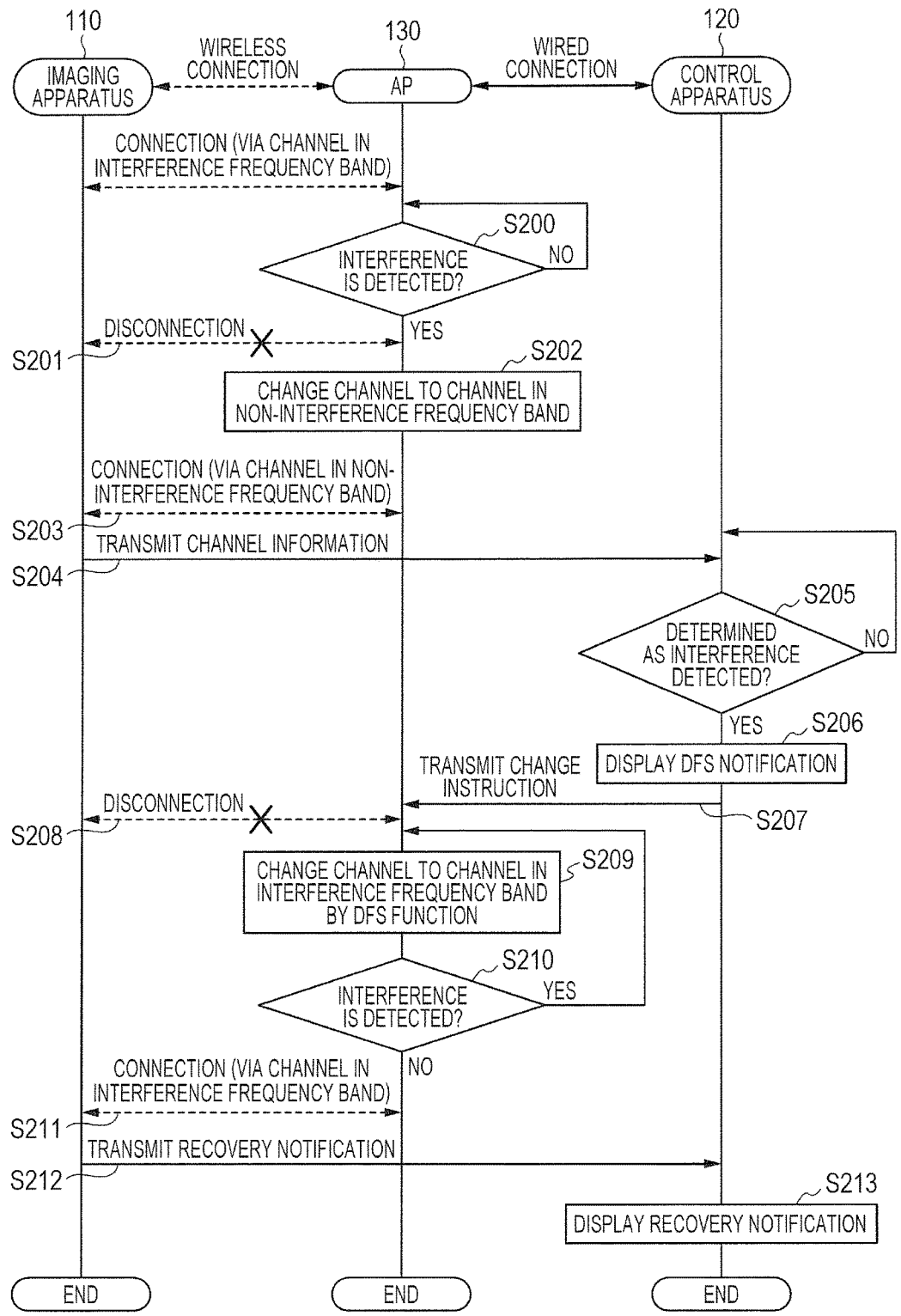

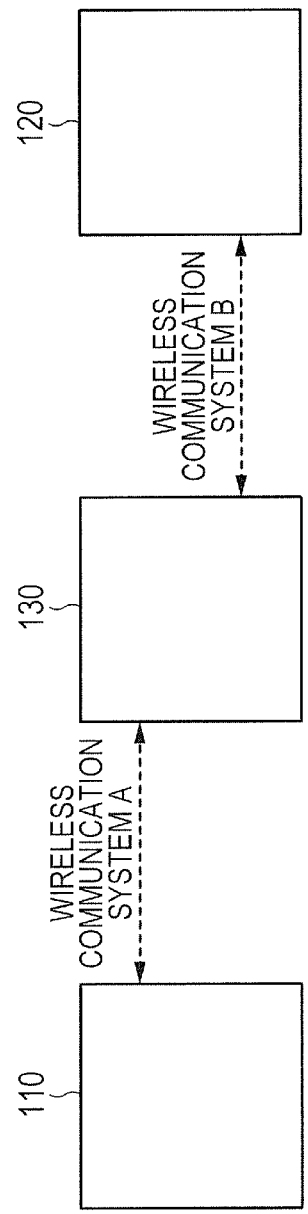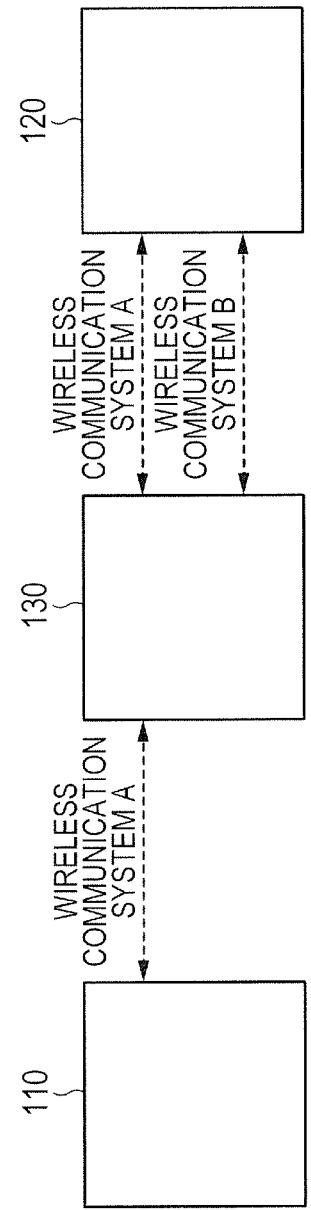

X-RAY IMAGING SYSTEM, INFORMATION PROCESSING METHOD, AND COMPUTER READABLE MEDIUM

BACKGROUND OF THE INVENTION

Field of the Invention

The present invention relates to an X-ray imaging system for acquiring an X-ray image of an object, an information processing method, and a computer readable medium having stored thereon a program for the X-ray imaging system and the information processing method.

Description of the Related Art

Hitherto, there has been known an X-ray imaging system including an imaging apparatus configured to receive an X-ray beam emitted by an X-ray generating apparatus to form an image and a control apparatus configured to control the imaging apparatus. In addition, for use in a medical cart, there has been widely used an X-ray imaging system in which the imaging apparatus and the control apparatus, which are wireless slave apparatus, are connected to an access point (a wireless master apparatus, hereinafter referred to as "AP") to communicate to/from each other.

A channel within a 5 GHz frequency band is sometimes used as a channel (a frequency band) for wireless communication in an X-ray imaging system. A part of the channels within the 5 GHz frequency band is a frequency band used by a meteorological radar or the like. Thus, when the AP uses this frequency band, the AP is required to support a dynamic frequency selection (DFS) function. In this case, the DFS function is a function of changing a channel to be used when detecting that the same channel is being used by the meteorological radar or the like in order to avoid interference with the meteorological radar or the like. In Japanese Patent No. 5708645, there is disclosed a technology relating to the DFS.

The DFS function disables communication after a channel is changed until it is confirmed that the meteorological radar or the like is not detected with the changed channel. However, there is a problem in that a user mistakes this phenomenon for an abnormality of the system without recognizing that the disabled communication is due to the DFS function.

SUMMARY OF THE INVENTION

The present invention has been made in view of the above-mentioned problem, and provides an X-ray imaging system capable of appropriately notifying a user of disabled communication due to a DFS function.

In view of the above, according to one embodiment of the present invention, there is provided an X-ray imaging system, including: an imaging apparatus configured to receive an X-ray beam to form an image; a control apparatus; a determination unit configured to determine whether or not interference with a specific device is detected in a channel used for wireless communication between at least one of the imaging apparatus or the control apparatus, and a master apparatus; and an output unit configured to output, when the interference is determined to have been detected and the wireless communication is stopped, notification information including a notification that the wireless communication is stopped, the imaging apparatus and the control apparatus being configured to communicate to/from each other via the wireless communication.

Further features of the present invention will become apparent from the following description of exemplary embodiments with reference to the attached drawings.

BRIEF DESCRIPTION OF THE DRAWINGS

FIG. 1 is an illustration of an imaging system.

FIG. 2 is a sequence diagram for illustrating communication control processing.

FIG. 8A and FIG. 8B are each an illustration of an imaging system according to a modified example of the fourth embodiment.

DESCRIPTION OF THE EMBODIMENTS

Figure 3A:
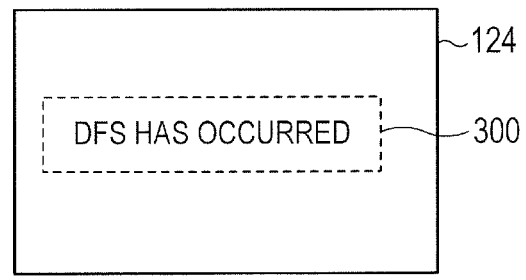
FIG. 3A and FIG. 3B are each an illustration of a display example of a display unit.

Preferred embodiments of the present invention will now be described in detail in accordance with the accompanying drawings.

First Embodiment

FIG. 1 is an illustration of an imaging system (X-ray imaging system) according to a first embodiment of the present invention. The imaging system includes an imaging apparatus 110, a control apparatus 120, and an access point (AP) apparatus 130. The AP apparatus 130 is an example of a master apparatus serving as a wireless master apparatus. The imaging apparatus 110 is an apparatus configured to receive an X-ray beam, which has been emitted by an X-ray generating apparatus and has passed through an object, to form an image, to thereby acquire an X-ray image. The imaging apparatus 110 has a function as a wireless slave apparatus, and connects to the AP apparatus 130 in a wireless manner. The control apparatus 120 is configured to control the imaging apparatus 110. The control apparatus 120 is also configured to receive an X-ray image acquired by the imaging apparatus 110 to display the image. The control apparatus 120 is connected to the AP apparatus 130 in a wired manner. In summary, the imaging apparatus 110 and the control apparatus 120 can communicate to/from each other via a wireless connection between the imaging apparatus 110 and the AP apparatus 130 and via a wired connection between the AP apparatus 130 and the control apparatus 120.

The imaging apparatus 110 includes a communication unit 111, a CPU 112, and a memory 113. The communication unit 111 has a function as a wireless slave apparatus, and is configured to communicate to/from another apparatus via the AP apparatus 130. The CPU 112 is configured to perform overall control of the imaging apparatus 110. The memory 113 is configured to store various kinds of information. The functions of and information processing by the imaging apparatus 110 according to this embodiment are implemented by the CPU 112 reading a program stored in the memory 113 and executing the program.

The control apparatus 120 includes a communication unit 121, a CPU 122, a memory 123, and a display unit 124. The communication unit 121 is configured to communicate to/from another apparatus via the AP apparatus 130 to which the communication unit 121 is connected in a wired manner. The CPU 122 is configured to perform overall control of the control apparatus 120. The memory 123 is configured to store various kinds of information. The display unit 124 is configured to display various kinds of information. The display unit 124 displays, for example, an X-ray image received from the imaging apparatus 110. The functions of and information processing by the control apparatus 120 according to this embodiment are implemented by the CPU 122 reading a program stored in the memory 123 and executing the program.

The AP apparatus 130 includes a wireless communication unit 131, a wired communication unit 132, a CPU 133, a memory 134, and a detection unit 135. The wireless communication unit 131 has a function as a wireless master apparatus, and is configured to communicate to/from an external apparatus in a wireless manner. The wired communication unit 132 is configured to communicate to/from the control apparatus 120 to which the wired communication unit 132 is connected in a wired manner. The CPU 133 is configured to perform overall control of the AP apparatus 130. The memory 134 is configured to store various kinds of information. The functions of and information processing by the AP apparatus 130 according to this embodiment are implemented by the CPU 133 reading a program stored in the memory 134 and executing the program.

The detection unit 135 is configured to detect a specific device that has caused interference with wireless communication of the wireless communication unit 131. In this embodiment, the wireless communication unit 131 uses any one of channels (frequency bands) within a 5 GHz frequency band for wireless communication, but a part of the channels within the 5 GHz frequency band is used by a meteorological radar or the like, which may cause interference with the meteorological radar or the like. Like the meteorological radar, the specific device is a device having a possibility of causing interference in a channel used for wireless communication of the wireless communication unit 131. In this embodiment, the detection unit 135 detects a specific device that has caused interference when such interference with the specific device has occurred.

Further, when interference with a specific device has occurred, the wireless communication unit 131 uses a dynamic frequency selection (DFS) function to change a channel used for wireless communication to another channel within the 5 GHz frequency band. In the following, a frequency band having a possibility of interfering with a specific device is referred to as an "interference frequency band". In contrast, a frequency band having no possibility of interfering with a specific device is referred to as a "non-interference frequency band". For example, W53 and W56 are interference frequency bands, and other frequency bands are non-interference frequency bands. The ranges of interference frequency bands and non-interference frequency bands are not limited to those in this embodiment.

FIG. 2 is a sequence diagram for illustrating communication control processing by the imaging system. In a usual state, the imaging apparatus 110 and the control apparatus 120 are in a state of being connected to each other for communication via the AP apparatus 130. The channel used for wireless communication by the AP apparatus 130 at this time is a channel in an interference frequency band. In this state, in Step S200, the detection unit 135 of the AP apparatus 130 detects whether or not interference with a specific device has occurred. When the detection unit 135 has detected interference with a specific device (YES in Step S200), the CPU 133 advances the processing to Step S201. In Step S201, the CPU 133 disables the AP function. Thus, wireless communication between the imaging apparatus 110 and the AP apparatus 130 is disconnected. Therefore, the communication between the imaging apparatus 110 and the control apparatus 120 via the AP apparatus 130 enters a disconnected state.

Next, in Step S202, the CPU 133 changes the channel for wireless communication by the wireless communication unit 131 to a channel in a non-interference frequency band. Then, in Step S203, the CPU 133 enables the AP function again. Thus, the communication between the imaging apparatus 110 and the control apparatus 120 via the AP apparatus 130 enters a connected state. At this time, the channel for wireless communication between the imaging apparatus 110 and the AP apparatus 130 becomes the channel in a non-interference frequency band set in Step S202. The changed channel is a channel in a non-interference frequency band, and thus there is no need for the AP apparatus 130 to monitor occurrence of interference with a specific device, resulting in a state in which the imaging apparatus 110 and the AP apparatus 130 can immediately connect to each other.

Meanwhile, the CPU 112 of the imaging apparatus 110 monitors the wireless communication state of the communication unit 111. Then, when the wireless communication state has changed from a connected state to a disconnected state, and then again to a connected state, the CPU 112 advances the processing to Step S204. In Step S204, the CPU 112 identifies the channel used for wireless communication before the disconnected state is entered and the channel used for wireless communication after the disconnected state is entered, namely, the channels before and after the disconnected state is entered. Then, the CPU 112 transmits to the control apparatus 120 channel information indicating the channels before and after the disconnected state is entered. As described above, when interference with a specific device is detected, the channel in an interference frequency band is changed to the channel in a non-interference frequency band. Therefore, the channel before the disconnected state is entered is the channel in an interference frequency band, and the channel after the disconnected state is entered is the channel in a non-interference frequency band.

In Step S204, when the CPU 122 of the control apparatus 120 receives channel information via the communication unit 121, the CPU 122 advances processing to Step S205. In Step S205, the CPU 122 determines whether or not the AP apparatus 130 has detected interference with a specific device based on the channel information. The memory 123 of the control apparatus 120 stores a table indicating channels in interference frequency bands and channels in non-interference frequency bands. Then, the CPU 122 refers to this table to find out which channels in interference frequency bands and non-interference frequency bands correspond to the channels before and after the disconnected state is entered, respectively, which are indicated by the channel information. Then, when the channel before the disconnected state is entered is a channel in an interference frequency band and the channel after the disconnected state is entered is a channel in a non-interference frequency band, the CPU 122 determines that interference with a specific device is detected. The CPU 122 waits until detection of interference with a specific device is determined (NO in Step S205), and when the CPU 122 determines that interference is detected (YES in Step S205), the CPU 122 advances the processing to Step S206.

In Step S206, the CPU 122 performs control such that the display unit 124 displays a DFS notification. In this case, the DFS notification is an example of notification information notifying a user of the fact that wireless communication is disabled and a non-communication state is entered due to the DFS function. Further, the processing of Step S206 is an example of output processing for outputting the notification information. FIG. 3A is an illustration of a display example of the DFS notification. In the example illustrated in FIG. 3A, text information indicating that "DFS has occurred" is displayed as a DFS notification 300.

Referring back to FIG. 2, after the processing of Step S206, the CPU 122 advances processing to Step S207. In Step S207, the CPU 122 transmits to the AP apparatus 130 via the communication unit 121 a change instruction indicating that the channel for wireless communication is to be changed from the channel in a non-interference frequency band to a channel in an interference frequency band, which is different from the already used channel in an interference frequency band. The processing order of Step S206 and Step S207 is not limited to the one described in this embodiment. In other cases, the CPU 122 may carry out the processing of Step S206 after the processing of Step S207, or may carry out the processing of Step S206 and the processing of Step S207 at the same time.

In Step S207, when the CPU 133 of the AP apparatus 130 receives the change instruction, the CPU 133 disables the AP function in Step S208. Thus, wireless communication between the imaging apparatus 110 and the AP apparatus 130 is disconnected. As a result, the communication between the imaging apparatus 110 and the control apparatus 120 via the AP apparatus 130 enters a disconnected state. Next, in Step S209, the CPU 133 changes the channel used for wireless communication to a channel in an interference frequency band in accordance with the change instruction using the DFS function. The channel in a non-interference frequency band is considered highly likely to interfere with a communication device other than the specific device. To address this issue, in this embodiment, the above-mentioned processing is carried out to achieve a minimum communication period in the channel in a non-interference frequency band.

Incidentally, the same channel as that in an interference frequency band that was used before detection of interference with a specific device in Step S200 is highly likely to interfere again with the specific device that has been detected in Step S200. Thus, the CPU 133 changes the channel for wireless communication to a channel that is in an interference frequency band and is different from the channel that was used before detection of the interference with the specific device. The AP apparatus 130 records the channel in an interference frequency band used by the AP apparatus 130 in, for example, a table in the memory 123. Then, in Step S208, the CPU 133 selects an unused channel that is not stored in the table and changes the channel for wireless communication to the selected channel. With this, it is possible to avoid selection of a channel that has actually caused interference in the past even when the AP apparatus 130 is rebooted.

Further, as another example, a plurality of imaging systems may carry out processing at the same time. In such a case, the table of each AP apparatus may store channels that do not interfere with the wireless communication of the AP apparatus of each imaging system as channels selectable by each AP apparatus. Then, each AP apparatus may select an unused channel among the channels selectable in interference frequency bands.

Next, in Step S210, the detection unit 135 carries out detection of interference with a specific device for a predetermined period of time. When the CPU 133 has detected interference with a specific device within the predetermined period of time (YES in Step S210), the CPU 133 advances the processing to Step S209, and changes the channel for wireless communication again. When the CPU 133 does not detect interference with a specific device for the predetermined period of time (No in Step S210), the CPU 133 advances the processing to Step S211. In Step S211, the CPU 133 enables the AP function again. As a result, the communication between the imaging apparatus 110 and the control apparatus 120 via the AP apparatus 130 enters a connected state. At this time, the channel for wireless communication between the imaging apparatus 110 and the AP apparatus 130 becomes the channel in an interference frequency band set in Step S209.

In Step S211, when the wireless communication state has changed from a disconnected state to a connected state again, the CPU 112 of the imaging apparatus 110 advances the processing to Step S212. In Step S212, the CPU 112 transmits a recovery notification to the control apparatus 120 via the communication unit 111. In this case, the recovery notification is information for notifying the user of the fact that the communication between the imaging apparatus 110 and the control apparatus 120 has resumed.

Figure 3B:
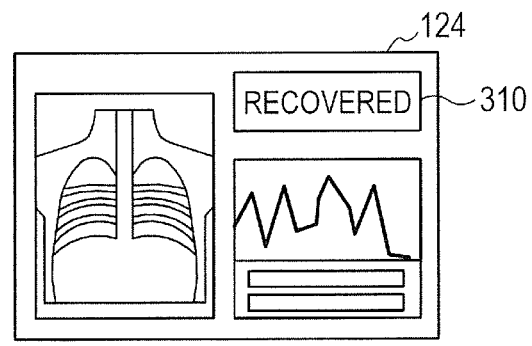

In Step S212, when the CPU 122 of the control apparatus 120 receives the recovery notification, the CPU 122 advances the processing to Step S213. In Step S213, the control apparatus 120 displays the recovery notification on the display unit 124. FIG. 3B is an illustration of a display example of the recovery notification. In the example illustrated in FIG. 3B, text information indicating "recovered" is displayed as a recovery notification 310 together with information, e.g., an X-ray image transmitted from the imaging apparatus 110. The communication control processing then finishes at this point.

As described above, in the imaging system according to the first embodiment, when the DFS function has caused a disabled state, it is possible to display a DFS notification on the display unit 124 of the control apparatus 120. In this manner, according to this embodiment, when the DFS function has caused a disabled state, it is possible to output notification information from an apparatus other than the AP apparatus 130. In other words, the imaging system according to this embodiment can appropriately notify the user of a disabled state due to the DFS function.

Figure 4:
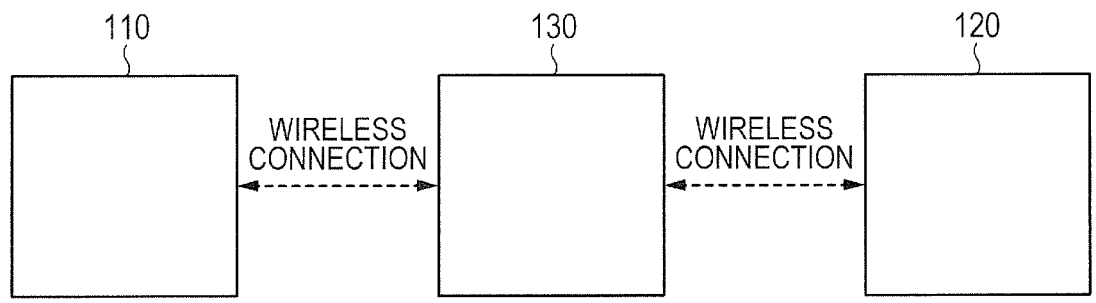
FIG. 4 is an illustration of an imaging system according to a first modified example of the present invention.

A first modified example of the first embodiment may be configured such that the communication between the control apparatus 120 and the AP apparatus 130 is implemented in a wireless manner instead of a wired manner, as shown in FIG. 4. In this case, the control apparatus 120 functions as a wireless slave apparatus to carry out wireless communication between the imaging apparatus 110 and the control apparatus 120 via the AP apparatus 130. Also in this case, the control apparatus 120, which is provided as a device separate from the AP apparatus, can output a DFS notification.

Further, as a second modified example of the first embodiment, the output mode for the DFS notification and the recovery notification by the control apparatus 120 is not limited to that of this embodiment. When the control apparatus 120 includes a speaker (not shown), the control apparatus 120 may output the DFS notification and the recovery notification as sound. Further, in other cases, when the control apparatus 120 includes a light emitting unit, e.g., an LED, the control apparatus 120 may output the DFS notification and the recovery notification by light emission of the light emitting unit.

Further, a third modified example of the first embodiment may be configured such that not only the control apparatus 120 but also the imaging apparatus 110 outputs the DFS notification. The imaging apparatus 110 includes a light emitting unit (not shown), and outputs the DFS notification by light emission of the light emitting unit. In this case, when detection of interference with a specific device is determined in Step S205 (YES in Step S205), the control apparatus 120 transmits a detection notification to the imaging apparatus 110. In this case, the detection notification is information indicating that interference with a specific device is detected. Then, when the imaging apparatus 110 receives the detection notification, the imaging apparatus 110 performs control such that the DFS notification is output as notification information. The output mode for the DFS notification by the imaging apparatus 110 is not limited to that of this embodiment. The imaging apparatus 110 may include, for example, a speaker serving as an output unit, and output the DFS notification by the speaker as sound.

Second Embodiment

Figure 5:
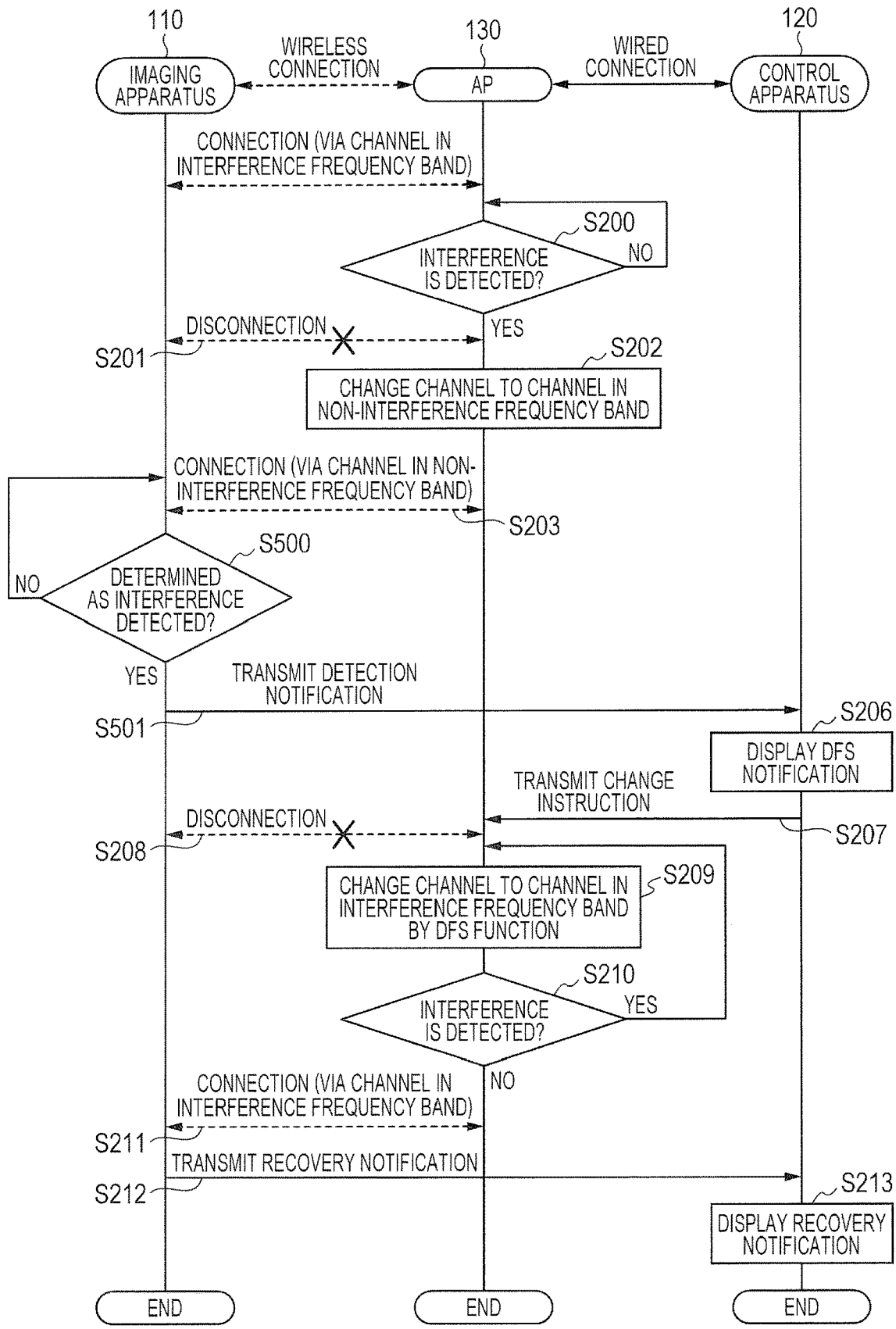
FIG. 5 is a sequence diagram for illustrating communication control processing according to a second embodiment of the present invention.

Next, a description is given of an imaging system according to a second embodiment of the present invention. In the imaging system according to the second embodiment, instead of the control apparatus 120, the imaging apparatus 110 determines detection of interference with a specific device. In the following, the imaging system according to the second embodiment is described focusing on differences from the imaging system according to the first embodiment. FIG. 5 is a sequence diagram for illustrating communication control processing according to the second embodiment. In FIG. 5, the same processing as that of the communication control processing of FIG. 2 is denoted by the same reference numeral.

In Step S203, the AP apparatus 130 enables the AP function again, and when the communication between the imaging apparatus 110 and the control apparatus 120 via the AP apparatus 130 enters a connected state, the CPU 112 of the imaging apparatus 110 advances the processing to Step S500. In Step S500, the CPU 112 determines whether or not the AP apparatus 130 has detected interference with a specific device based on the channels before and after the disconnected state is entered. This processing is the same as the processing of Step S205 illustrated in FIG. 2. It is assumed that the memory 113 of the imaging apparatus 110 stores a table indicating channels in interference frequency bands and channels in non-interference frequency bands.

The CPU 112 waits until detection of interference with a specific device is determined (NO in Step S500), and when the CPU 112 determines that interference is detected (YES in Step S500), the CPU 112 advances the processing to Step S501. In Step S501, the imaging apparatus 110 transmits a detection notification to the control apparatus 120. When the CPU 122 of the control apparatus 120 receives the detection notification, the CPU 122 advances the processing to Step S206. The configuration and processing other than those described above of the imaging system according to the second embodiment are similar to the configuration and processing of the imaging system according to the first embodiment. Also in this embodiment, the imaging system can appropriately notify the user of a disabled state due to the DFS function.

Also in the second embodiment, as described in the first modified example of the first embodiment, the communication between the control apparatus 120 and the AP apparatus 130 may be implemented in a wireless manner instead of a wired manner. Further, the second and third modified examples of the first embodiment may be applied to the imaging system according to the second embodiment.

Third Embodiment

Figure 6:
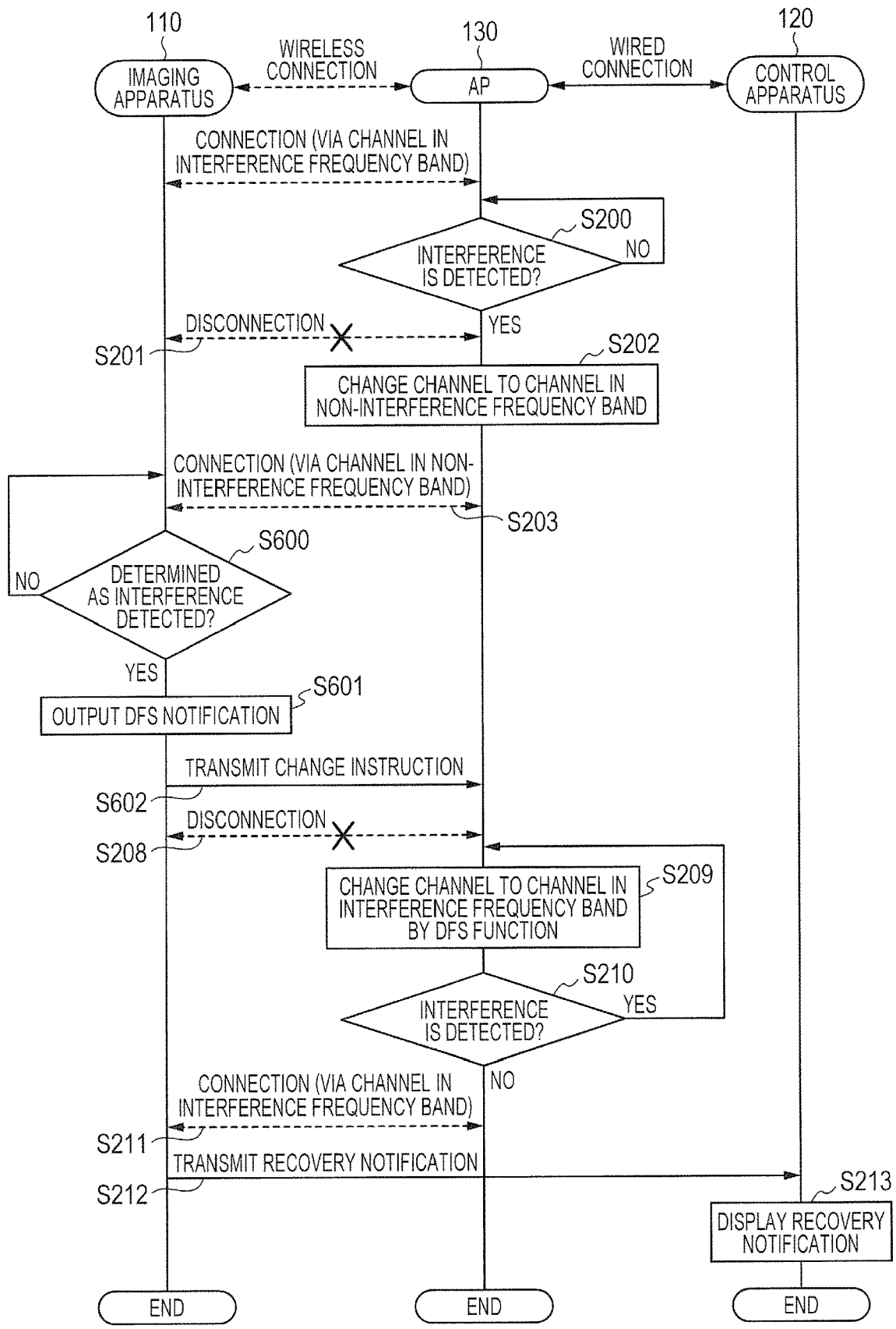
FIG. 6 is a sequence diagram for illustrating communication control processing according to a third embodiment of the present invention.

Next, a description is given of an imaging system according to a third embodiment of the present invention. In the imaging system according to the third embodiment, only the imaging apparatus 110 outputs a DFS notification, and the control apparatus 120 does not display a DFS notification. It is assumed that the imaging apparatus 110 includes an output unit, e.g., a light emitting unit. The output unit of the imaging apparatus 110 is configured as described in the third modified example of the first embodiment. The imaging apparatus 110 determines detection of interference with a specific device and outputs a DFS notification. In the following, a description is given of the imaging system according to the third embodiment focusing on differences from the imaging systems according to the other embodiments. FIG. 6 is a sequence diagram for illustrating communication control processing according to the third embodiment.

In Step S203, the AP apparatus 130 enables the AP function again, and when the communication between the imaging apparatus 110 and the control apparatus 120 via the AP apparatus 130 enters a connected state, the CPU 112 of the imaging apparatus 110 advances the processing to Step S600. In Step S600, the CPU 112 determines whether or not the AP apparatus 130 has detected interference with a specific device based on the channels before and after the disconnected state is entered. This processing is the same as the processing of Step S205 illustrated in FIG. 2. It is assumed that the memory 113 of the imaging apparatus 110 stores a table indicating channels in interference frequency bands and channels in non-interference frequency bands.

The CPU 112 waits until detection of interference with a specific device is determined (NO in Step S600), and when the CPU 112 determines that interference with a specific device is detected (YES in Step S600), the CPU 112 advances the processing to Step S601. In Step S601, the CPU 112 performs control such that a DFS notification is output. Next, in Step S602, the CPU 112 transmits a change instruction to the AP apparatus 130 via the communication unit 111. After that, the AP apparatus 130 carries out the processing of Step S208 onward. The processing order of Step S601 and Step S602 is not limited to the one described in this embodiment. The configuration and processing other than those described above of the imaging system according to the third embodiment are similar to the configuration and processing of the imaging systems according to the other embodiments.

As described above, when an apparatus (control apparatus 120) that is connected to the AP apparatus 130 in a wired manner does not need to output a DFS notification, an apparatus (imaging apparatus 110) that is connected to the AP apparatus 130 in a wireless manner may determine detection of interference with a specific device and output a DFS notification.

Also in the third embodiment, as described in the first modified example of the first embodiment, the communication between the control apparatus 120 and the AP apparatus 130 may be implemented in a wireless manner instead of a wired manner.

Fourth Embodiment

Figure 7:
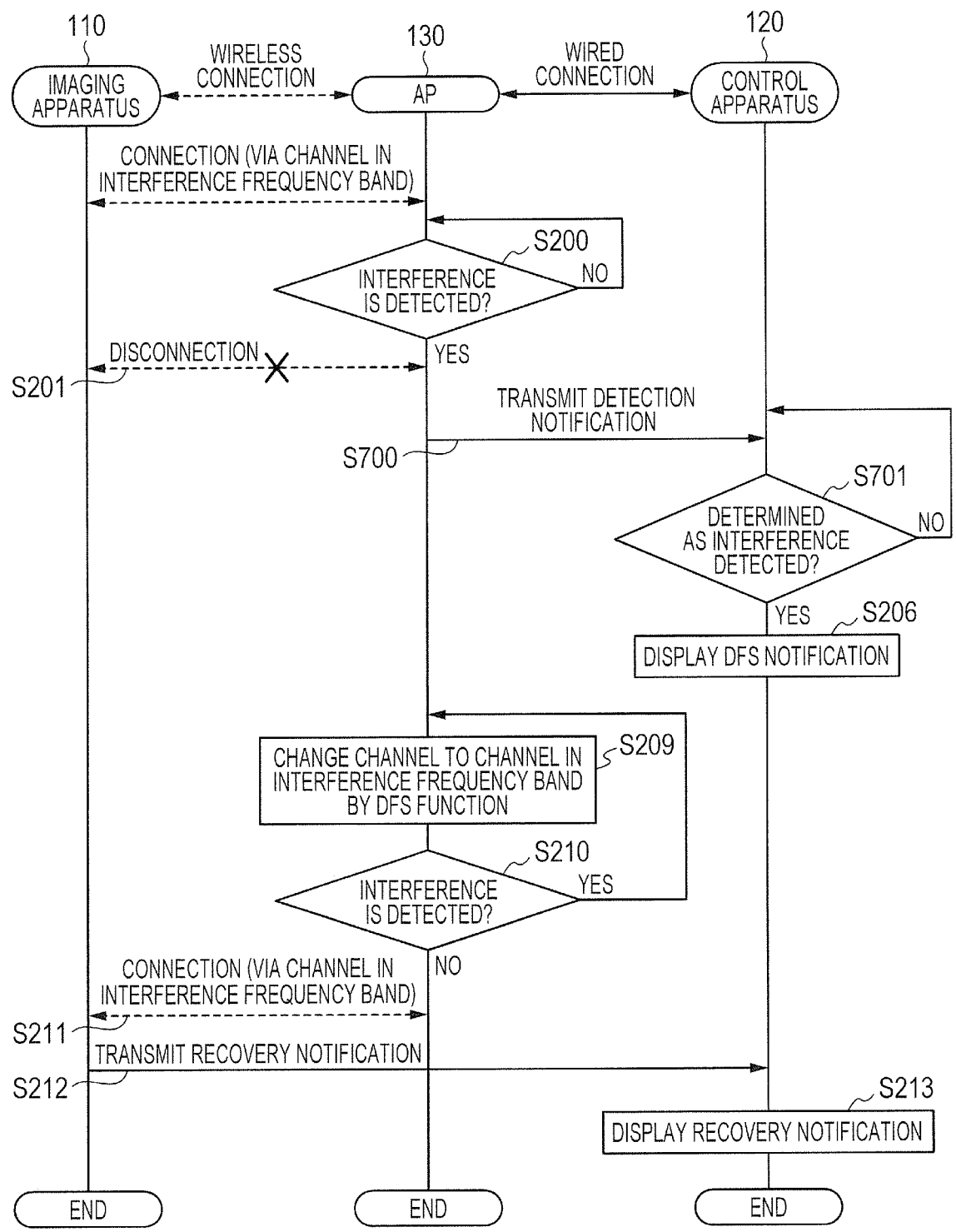
FIG. 7 is a sequence diagram for illustrating communication control processing according to a fourth embodiment of the present invention.

Next, a description is given of an imaging system according to a fourth embodiment of the present invention. In the imaging system according to the fourth embodiment, when the AP apparatus 130 has detected interference with a specific device, the control apparatus 120 receives a notification from the AP apparatus 130, and displays a DFS notification based on this notification. In the following, the imaging system according to the fourth embodiment is described focusing on differences from the imaging system according to the other embodiments. FIG. 7 is a sequence diagram for illustrating communication control processing according to the fourth embodiment.

In Step S200, when the CPU 133 of the AP apparatus 130 has detected interference with a specific device, in Step S201, the CPU 133 disables the AP function, and then advances the processing to Step S700. In Step S700, the CPU 133 transmits a detection notification to the control apparatus 120 via the wired communication unit 132. The processing order of Step S700 and Step S201 is not limited to the one described in this embodiment. In Step S701, the CPU 122 of the control apparatus 120 determines detection of interference with a specific device. When the CPU 122 receives a detection notification, the CPU 122 determines that interference with a specific device is detected. The CPU 122 waits until detection of interference with a specific device is determined (NO in Step S701), and when the CPU 122 determines that interference with a specific device is detected (YES in Step S701), the CPU 122 advances the processing to Step S206. Then, in Step S206, the CPU 122 displays a DFS notification.

As described above, in this embodiment, the AP apparatus 130 transmits a detection notification to the control apparatus 120 via wired communication, and thus the control apparatus 120 can determine whether or not interference with a specific device is detected without receiving channel information from the imaging apparatus 110. Therefore, in this embodiment, processing of changing the interference frequency to the non-interference frequency (Step S202) and transmitting channel information (Step S203) in the communication control processing of the first embodiment is unnecessary.

Then, in Step S700, the CPU 133 of the AP apparatus 130 transmits a detection notification, and then advances the processing to Step S209 to use the DFS function to change the channel used for wireless communication to a channel in an interference frequency band. The configuration and processing other than those described above of the imaging system according to the fourth embodiment are similar to the configuration and processing of the imaging systems according to the other embodiments.

As described above, when the AP apparatus 130 can transmit a detection notification to an apparatus (control apparatus 120) to which the AP apparatus 130 is connected in a wired manner, the control apparatus 120 can determine that interference with a specific device is detected by receiving the detection notification, and output a DFS notification.

The communication between the control apparatus 120 and the AP apparatus 130 is not limited to wired communication. It suffices that a modified example of the fourth embodiment is configured such that the control apparatus 120 and the AP apparatus 130 communicate to/from each other by a communication method other than the wireless communication between the imaging apparatus 110 and the AP apparatus 130. As the method other than the wireless communication between the imaging apparatus 110 and the AP apparatus 130, as illustrated in FIG. 8A, a wireless communication method (wireless communication method B), which is different from the method of wireless communication between the imaging apparatus 110 and the AP apparatus 130 (wireless communication method A) may be employed. As the wireless communication method B, for example, wireless communication such as infrared communication or Bluetooth (trademark) may be employed. Further, as another example, as illustrated in FIG. 8B, connection by the wireless communication method A and connection by the wireless communication method B may both be established between the control apparatus 120 and the AP apparatus 130. In this case, when the control apparatus 120 receives an X-ray image, the control apparatus 120 may use communication by the wireless communication method A, whereas when the control apparatus 120 receives a detection notification, the control apparatus 120 may use communication by the wireless communication method B.

Fifth Embodiment

Next, a description is given of an imaging system according to a fifth embodiment of the present invention. In the imaging system according to the fifth embodiment, when the AP apparatus 130 changes the channel for wireless communication from a channel in an interference frequency band to a channel in a non-interference frequency band, the control apparatus 120 receives channel information from the AP apparatus 130. Then, the control apparatus 120 determines detection of interference with a specific device in accordance with channel information. Then, when the control apparatus 120 determines that interference with a specific device is detected, the control apparatus 120 transmits a detection notification to the imaging apparatus 110, and the imaging apparatus 110 outputs a DFS notification based on the detection notification.

Figure 9:
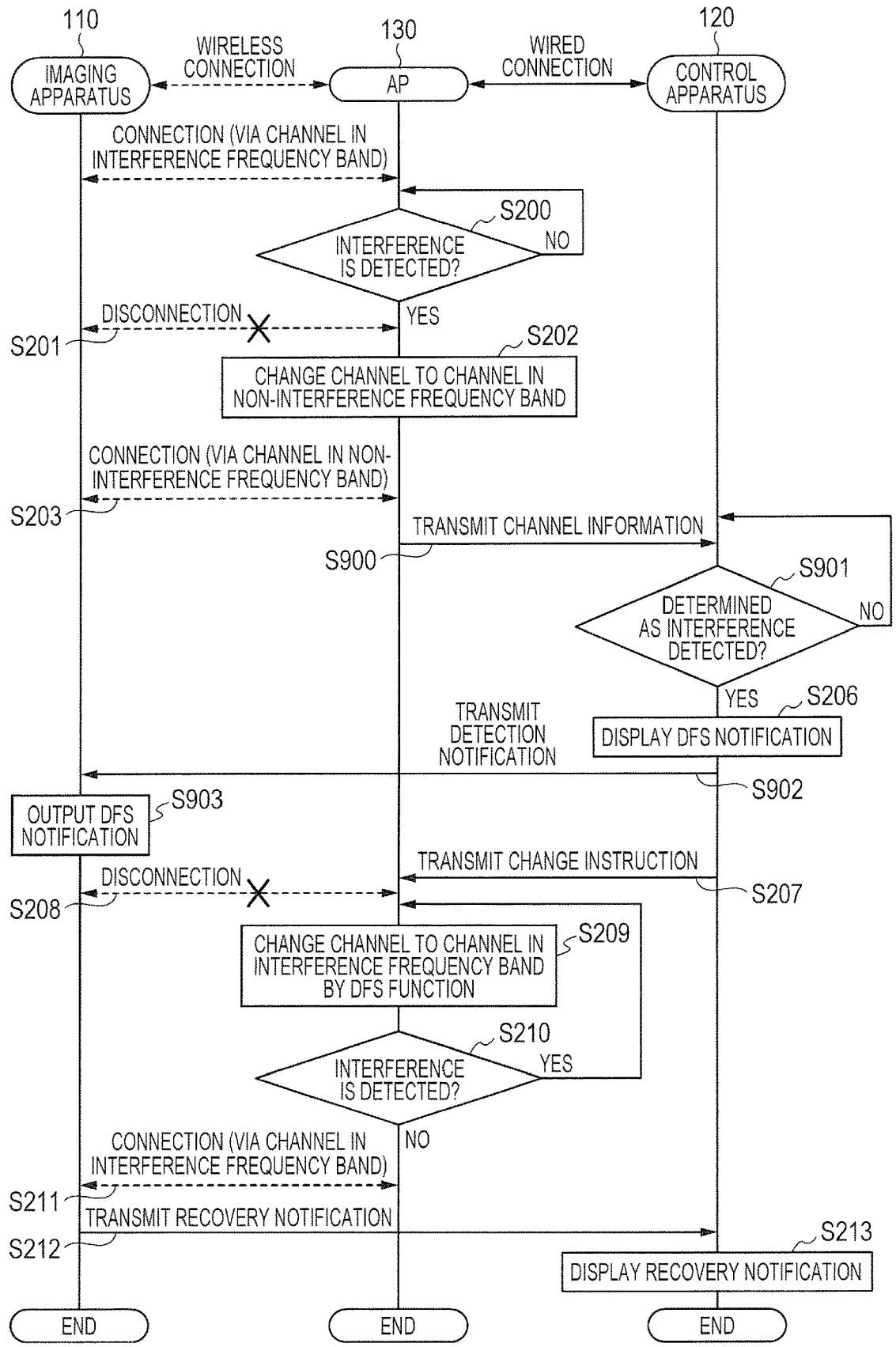
FIG. 9 is a sequence diagram for illustrating communication control processing according to a fifth embodiment of the present invention.

In the following, the imaging system according to the fifth embodiment is described focusing on differences from the imaging systems according to the other embodiments. FIG. 9 is a sequence diagram for illustrating communication control processing according to the fifth embodiment. In Step S203, the CPU 133 of the AP apparatus 130 enables the AP function again, and then, in Step S900, transmits channel information to the control apparatus 120.

Meanwhile, in Step S901, the CPU 122 of the control apparatus 120 determines detection of interference with a specific device. When the CPU 122 determines that interference with a specific device is detected (YES in S901) based on the channel information, the CPU 122 advances the processing to Step S206. Then, in Step S206, the CPU 122 performs control such that a DFS notification is displayed, and advances the processing to Step S902. In Step S902, the CPU 122 transmits a detection notification to the imaging apparatus 110, and then advances the processing to Step S207. The processing order of Step S902, Step S206, and Step S207 is not limited to the one described in this embodiment.

In Step S902, when the CPU 112 of the imaging apparatus 110 receives the detection notification, the CPU 112 advances the processing to Step S903. In Step S903, the CPU 112 performs control such that the DFS notification is output. The configuration and processing other than those described above of the imaging system according to the fifth embodiment are similar to the configuration and processing of the imaging systems according to the other embodiments.

As described above, when the control apparatus 120, which is connected to the AP apparatus 130 in a wired manner, outputs a detection notification to the imaging apparatus 110, which is connected to the AP apparatus 130 in a wireless manner, the channel used for wireless communication between the imaging apparatus 110 and the AP apparatus 130 is changed to a channel in a non-interference frequency band. With this, the control apparatus 120 can transmit a detection notification to the imaging apparatus 110 via wireless communication through the channel in a non-interference frequency band, and the imaging apparatus 110 can output a DFS notification in accordance with the detection notification.

A modified example of the fifth embodiment may be configured such that the processing of Step S206 is omitted when a DFS notification is unnecessary in the control apparatus 120.

Further, a description is now given of modified examples of the first to fifth embodiments described above. In the first to fifth embodiments, the imaging apparatus 110 and the AP apparatus 130 are connected to each other in a wireless manner, and the control apparatus 120 and the AP apparatus 130 are connected to each other in a wired manner. In contrast, in the modified examples, the imaging apparatus 110 and the AP apparatus 130 may be connected to each other in a wired manner, and the control apparatus 120 and the AP apparatus 130 may be connected to each other in a wireless manner. Further, in the imaging systems according to the modified examples, regarding the communication control processing in each embodiment, the control apparatus 120 may carry out processing that is described above as being carried out by the imaging apparatus 110, and the imaging apparatus 110 may carry out processing that is described above as being carried out by the control apparatus 120. Also in this case, the imaging apparatus 110, which is provided as an apparatus separate from the AP apparatus, can output a DFS notification.

In other words, in the modified example of the first embodiment, the control apparatus 120 transmits channel information to the imaging apparatus 110 (Step S204) in the communication control processing (FIG. 2). Then, the imaging apparatus 110 determines detection of interference with a specific device (Step S205), displays a DFS notification (Step S206), and transmits a change instruction (Step S207).

Further, in the modified example of the second embodiment, the control apparatus 120 determines detection of a specific device (Step S500) and transmits a detection notification (Step S501) in the communication control processing (FIG. 5). Then, the imaging apparatus 110 displays a DFS notification (Step S206) and transmits a change instruction (Step S207).

Further, in the modified example of the third embodiment, the control apparatus 120 determines detection of a specific device (Step S600), outputs a DFS notification (Step S601), and transmits a change instruction (Step S602) in the communication control processing (FIG. 6).

Further, in the modified example of the fourth embodiment, the AP apparatus 130 transmits a detection notification to the imaging apparatus 110 (Step S700), and the imaging apparatus 110 determines detection of a specific device (Step S701) and outputs a DFS notification (Step S206) in the communication control processing (FIG. 7).

Further, in the modified example of the fifth embodiment, the AP apparatus 130 transmits channel information to the imaging apparatus 110 (Step S900), and the imaging apparatus 110 determines detection of a specific device (Step S901) and transmits detection information (Step S902) in the communication control processing (FIG. 9).

Further, regarding the first to third embodiments, the communication control processing of the modified examples described above in which wired communication and wireless communication are switched can be applied to the configuration in which the imaging apparatus 110 and the AP apparatus 130 are connected to each other in a wireless manner, and the AP apparatus 130 and the control apparatus 120 are also connected to each other in a wireless manner.

Further, in the embodiments described above, a description is given of a configuration in which the AP apparatus 130 functions as a wireless master apparatus. However, the configuration of the present invention is not limited to this. For example, a configuration may be adopted in which the imaging apparatus 110 functions as a wireless master apparatus and the control apparatus 120 functions as a wireless slave apparatus to allow those apparatus to connect to each other in a wireless manner.

As described above, according to the above-mentioned embodiments, it is possible to appropriately notify the user of the disabled communication due to the DFS function.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-041311, filed Mar. 3, 2016, which is hereby incorporated by reference herein in its entirety.

What is claimed is:

1. An X-ray imaging system comprising:
    an imaging apparatus configured to receive an X-ray beam to form an image;
    a control apparatus;
    a determination unit configured to determine whether or not interference with a specific device is detected in a channel used for wireless communication between at least one of the imaging apparatus or the control apparatus, and a master apparatus; and
    an output unit configured to output, when the interference is determined to have been detected and the wireless communication is stopped, notification information including a notification that the wireless communication is stopped,
    wherein the imaging apparatus and the control apparatus are configured to communicate with each other via the wireless communication,
    wherein the imaging apparatus is connected to the master apparatus in a wireless manner as a wireless slave apparatus,
    wherein the imaging apparatus is configured to transmit to the control apparatus, when communication to/from the control apparatus via the master apparatus has entered a disconnected state from a connected state and then entered a connected state again, channel information for indicating channels used for wireless communication before and after the disconnected state is entered,
    wherein the control apparatus comprises the determination unit, and
    wherein the determination unit is configured to determine that the interference is detected when the determination unit refers to the channel information received from the imaging apparatus to find out that the channel before the disconnected state is entered is a channel having a possibility of interfering with the specific device and the channel after the disconnected state is entered is a channel having no possibility of interfering with the specific device.

2. The X-ray imaging system according to claim 1, further comprising a first transmission unit configured to transmit to the master apparatus, after the determination unit determines that the interference is detected, a change instruction for changing the channel used for the wireless communication from the channel after the disconnected state is entered to a channel of an interference frequency and different from the channel before the disconnected state is entered.

3. The X-ray imaging system according to claim 1, wherein the control apparatus is connected to the master apparatus in a wired manner, and
    wherein the imaging apparatus and the control apparatus are configured to communicate to/from each other via wired communication between the control apparatus and the master apparatus and via wireless communication between the imaging apparatus and the master apparatus.

4. The X-ray imaging system according to claim 1, wherein the control apparatus is connected to the master apparatus in a wireless manner as a wireless slave apparatus, and
    wherein the control apparatus is configured to transmit a detection notification to the imaging apparatus when the determination unit determines that the interference is detected.

5. The X-ray imaging system according to claim 1, wherein the control apparatus is connected to the master apparatus in a wireless manner as a wireless slave apparatus, and
    wherein the control apparatus comprises the determination unit and the output unit.

6. An X-ray imaging system comprising:
    an imaging apparatus configured to receive an X-ray beam to form an image; and
    a control apparatus,
    the imaging apparatus comprising a communication unit configured to function as a wireless master apparatus and communicate to/from the control apparatus in a wireless manner,
    the control apparatus comprising:
        a communication unit configured to function as a wireless slave device and communicate to/from the imaging apparatus in a wireless manner;
        a determination unit configured to determine whether or not interference with a specific device is detected in a channel used for the wireless communication; and
        an output unit configured to output, when the interference is determined to have been detected and the wireless communication is stopped, notification information including a notification that the wireless communication is stopped,
    wherein the imaging apparatus is configured to transmit to the control apparatus, when communication to/from the control apparatus has entered a disconnected state from a connected state and then entered a connected state again, channel information for indicating channels used for wireless communication before and after the disconnected state is entered, and
    wherein the determination unit is configured to determine that the interference is detected when the determination unit refers to the channel information received from the imaging apparatus to find out that the channel before the disconnected state is entered is a channel having a possibility of interfering with the specific device and the channel after the disconnected state is entered is a channel having no possibility of interfering with the specific device.

7. An information processing method to be executed by an X-ray imaging system,
    the X-ray imaging system comprising:
        an imaging apparatus configured to receive an X-ray beam to form an image; and
        a control apparatus, the imaging apparatus and the control apparatus being configured to communicate to/from each other via wireless communication between at least one of the imaging apparatus or the control apparatus, and a master apparatus,
    the information processing method comprising:
        determining whether or not interference with a specific device is detected in a channel used for the wireless communication; and
        outputting, when the interference is determined to have been detected and the wireless communication is stopped, notification information including a notification that the wireless communication is stopped,
    wherein the imaging apparatus is connected to the master apparatus in a wireless manner as a wireless slave apparatus,
    wherein the imaging apparatus is configured to transmit to the control apparatus, when communication to/from the control apparatus via the master apparatus has entered a disconnected state from a connected state and then entered a connected state again, channel information for indicating channels used for wireless communication before and after the disconnected state is entered, wherein the control apparatus comprises a determination unit, and wherein in the determining, it is determined that the interference is detected when the determination unit refers to the channel information received from the imaging apparatus to find out that the channel before the disconnected state is entered is a channel having a possibility of interfering with the specific device and the channel after the disconnected state is entered is a channel having no possibility of interfering with the specific device.

8. The X-ray imaging system according to claim 1, wherein the determination unit is configured to determine that the interference is detected in accordance with channel information indicating the switching of the channel used for communication from the channel before the disconnected state is entered to the channel after the disconnected state is entered.

* * * * *